United States Patent
Volz et al.

(10) Patent No.: US 11,638,670 B1
(45) Date of Patent: May 2, 2023

(54) SYSTEMS AND METHODS FOR MAINTAINING PATIENT POSITION

(71) Applicant: Volz Surgical Consulting Inc., Dakota Dunes, SD (US)

(72) Inventors: Lawrence T. Volz, Dakota Dunes, SD (US); Adam Troness, Dellwood, MN (US); Richard A. Thompson, II, Saint Louis Park, MN (US); Jacob Wilson, Blaine, MN (US); Ryan Lawrence Smith, Woodbury, MN (US)

(73) Assignee: Volz Surgical Consulting Inc., Dakota Dunes, SD (US)

( * ) Notice: Subject to any disclaimer, the term of this patent is extended or adjusted under 35 U.S.C. 154(b) by 0 days.

(21) Appl. No.: 17/827,098

(22) Filed: May 27, 2022

(51) Int. Cl.
*A61G 13/02* (2006.01)
*A61G 13/00* (2006.01)

(52) U.S. Cl.
CPC ......... *A61G 13/02* (2013.01); *A61G 13/0036* (2013.01); *A61G 2200/322* (2013.01); *A61G 2200/325* (2013.01); *A61G 2200/327* (2013.01)

(58) Field of Classification Search
CPC ............... A61G 13/02; A61G 13/0036; A61G 2200/322; A61G 2200/325; A61G 2200/327; A61B 17/02; A61F 5/37
See application file for complete search history.

(56) References Cited

U.S. PATENT DOCUMENTS

| | | | | |
|---|---|---|---|---|
| 2,245,293 A | * | 6/1941 | Ogburn | A61F 5/3761 128/882 |
| 2,510,198 A | * | 6/1950 | Tesmer | B25B 5/006 248/231.71 |
| 3,096,962 A | * | 7/1963 | Meijs | G05G 5/06 138/120 |
| 3,168,274 A | * | 2/1965 | Street | B25H 1/005 248/176.3 |
| 3,858,578 A | * | 1/1975 | Milo | A61B 17/02 600/230 |
| 4,239,036 A | * | 12/1980 | Krieger | A61B 17/02 600/206 |
| 4,473,912 A | * | 10/1984 | Scheidel | A61G 1/044 5/628 |
| 4,729,138 A | * | 3/1988 | Heyman | A61G 7/05 248/231.71 |

(Continued)

OTHER PUBLICATIONS universalmedicalinc.com [online], "Deluxe Arthroscopic Legholder System," 1983, retrieved on Jul. 12, 2022, retrieved from URL<https://www.universalmedicalinc.com/deluxe-arthroscopic-legholder-system.html>, 7 pages.

*Primary Examiner* — Myles A Throop
(74) *Attorney, Agent, or Firm* — Fish & Richardson P.C.

(57) ABSTRACT

Some systems, devices and methods detailed herein provide adjustable restraint device maintaining a selected position of a person relative to a support structure, for example, to maintain a safe and customizable patient position during a surgical procedure or during medical transport. For example, in particular embodiments, the adjustable restraint devices can be releasably lockable at a customized position along the surgical table and can be conveniently manipulated to a curved or other customized configuration (e.g., to engage with a patient's limb) before being releasably locked into that particular customized configuration.

21 Claims, 11 Drawing Sheets

(56) References Cited

U.S. PATENT DOCUMENTS

| | | | | |
|---|---|---|---|---|
| 5,348,259 A | * | 9/1994 | Blanco | F16M 11/40 |
| | | | | 403/56 |
| 7,730,565 B1 | * | 6/2010 | Masson | A61G 1/04 |
| | | | | 5/503.1 |
| 8,870,141 B2 | | 10/2014 | Abri et al. | |
| 11,079,807 B1 | | 8/2021 | Robinson et al. | |
| 2001/0044967 A1 | * | 11/2001 | Gaspar | A61G 1/04 |
| | | | | 5/632 |
| 2011/0038064 A1 | | 2/2011 | Xhunga | |
| 2020/0000623 A1 | | 1/2020 | Allen | |

* cited by examiner

SYSTEMS AND METHODS FOR MAINTAINING PATIENT POSITION

TECHNICAL FIELD

This disclosure describes systems, devices, and methods for releasably and safely retaining a subject, such as a patient during surgical procedures or during transport to a medical site. Particular examples described herein provide improved positioning and releasable restraint of one or more limbs of a patient in a customizable and safe position while the patient is sedated during a surgical procedure.

BACKGROUND

Maintaining a consistent and safe position of a patient during a surgical procedure facilitates improved surgical outcomes and reduces the likelihood of inadvertent limb movement and consequences thereof, such as paresthesia or ischemia in a limb that inadvertently shifted positions during the course of a surgery. For example, in some circumstances when a patient can be subjected to anesthesia during a surgical procedure, the patient may not be able to control or position themselves or otherwise alert the medical practitioner of discomfort or paresthesia in a limb. Medical practitioners have employed a number of techniques to control the position of the patient during a medical procedure. For example, some medical staff may utilize folding or cushioning techniques of the sheets on the operating table to hold the patient in position. These techniques can include wrapping a sheet around a patient's limb and into a cushion of the surgical table to hold the patient's limb in position during the procedure. Such a technique can be ineffective at maintaining a consistent and safe position of the patient throughout a procedure because the sheets can loosen in some areas, allowing a limb of the patient to move from the originally selected position. Additionally, in some circumstances involving an obese or oversized patient that occupies areas larger than the surgical table, such conventional techniques may fail to safely retain the patient's limbs in a consistent and safe manner throughout the duration of the medical procedure.

SUMMARY

This disclosure describes systems, devices, and methods for maintaining a selected position of a person relative to a support structure, for example, to achieve a safe and customizable patient position during a surgical procedure or during medical transport of a patient. In particular implementations, the systems, devices, and methods described herein can include at least one adjustable restraint devices that achieves improved adjustability for releasably capturing of one or more portions of a patient in a safe position relative to a surgical operating table or medical transport device.

Among other benefits, some systems and methods described herein can advantageously provide a more efficient and customizable approach to maintain any of a wide variety of patient sizes in a selected position a surgical operating table or medical transport device. For example, in particular embodiments, the adjustable restraint devices can be releasably lockable at a customized position along the surgical table and can be conveniently manipulated to a curved or other customized configuration (e.g., to engage with a patient's limb) before being releasably locked into that particular customized configuration. Additionally, some embodiments described in more detail below can achieve a removable, reusable solution that provides added comfort to a patient engaged with the adjustable restraint device while also achieving efficient disposable of particular components and reuse of other more complex components.

Some embodiments described herein include a flexible cuff system for releasably maintaining a position of a patient. The system can include a flexible cuff body adjustable from a first orientation to a customized orientation to retain a limb in a selected position relative to a medical support substrate. Also, the system may optionally include a handle body connected to a base portion of the flexible cuff body, the handle body including a handle that is movable between a locked position and an unlocked position, and the handle body defining a mating interface surface that to slidably engage the medical support substrate. In particular circumstances, responsive to the handle being moved to the unlocked position, the flexible cuff body can be adjustable from the first orientation to the customized orientation to extend around the limb. Also, in some circumstances, responsive to the handle being moved to the locked position while the flexible cuff body is in the customized orientation, the flexible cuff body can be locked in the customized orientation to retain the limb in the selected position relative to the medical support substrate.

A number of embodiments described herein include a system that includes a plurality of adjustable limb restraints. The system may optionally include a surgical table including one or more rails that extend along one or more sides of the surgical table. The plurality of adjustable limb restraints may be releasably lockable at selectable positions along the one or more rails of the surgical table. Each of the adjustable limb restraints may include a flexible cuff body adjustable from a first orientation to a customized orientation to retain a limb in a customized position relative to the surgical table. Also, each of the adjustable limb restraints may include a handle body connected to a base of the flexible cuff body. The handle body can include a handle movable between a locked position and an unlocked position. Optionally, the handle body may define a mating interface surface to slidably engage at least one of the one or more rails. Responsive to the handle being moved to the unlocked position, the flexible cuff body can be adjustable from the first orientation to the customized orientation to extend around the limb. Further, responsive to the handle being moved to the locked position while the flexible cuff body is in the customized orientation, the flexible cuff body can be locked in the customized orientation to retain the limb in the selected position relative to the surgical table.

Some embodiments described herein include a method of maintaining a position of a patient. The method may include releasably locking a handle body of an adjustable limb restraint to a rail of an operating table at a selected location relative to a limb of a patient on the operating table. The method may further include adjusting a flexible cuff body of the adjustable limb restraint to a selected shape to engage with the limb of the patient. Also, the method may include adjusting an actuator on the handle body of the adjustable limb restraint to releasably lock the flexible cuff body in the selected shape.

Particular implementations can, in certain instances, realize one or more of the following advantages. The systems, devices, and methods described herein provide a more secure and consistent approach to holding patients and patient limbs in position on a surgical table or medical transport device that reduces the likelihood that a patient or a patient limb may move out of the desirable position and maintains the original position of the patient or patient limb during the procedure or transport. Additionally, the presently described systems, devices, and methods offer a removable, reusable solution that is advantageously adjustable to capture patients and portions of patients of various sizes and is readily adjustable to engage with different sizes and shapes of patients or patient limbs.

The details of one or more implementations are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

Figure 1:
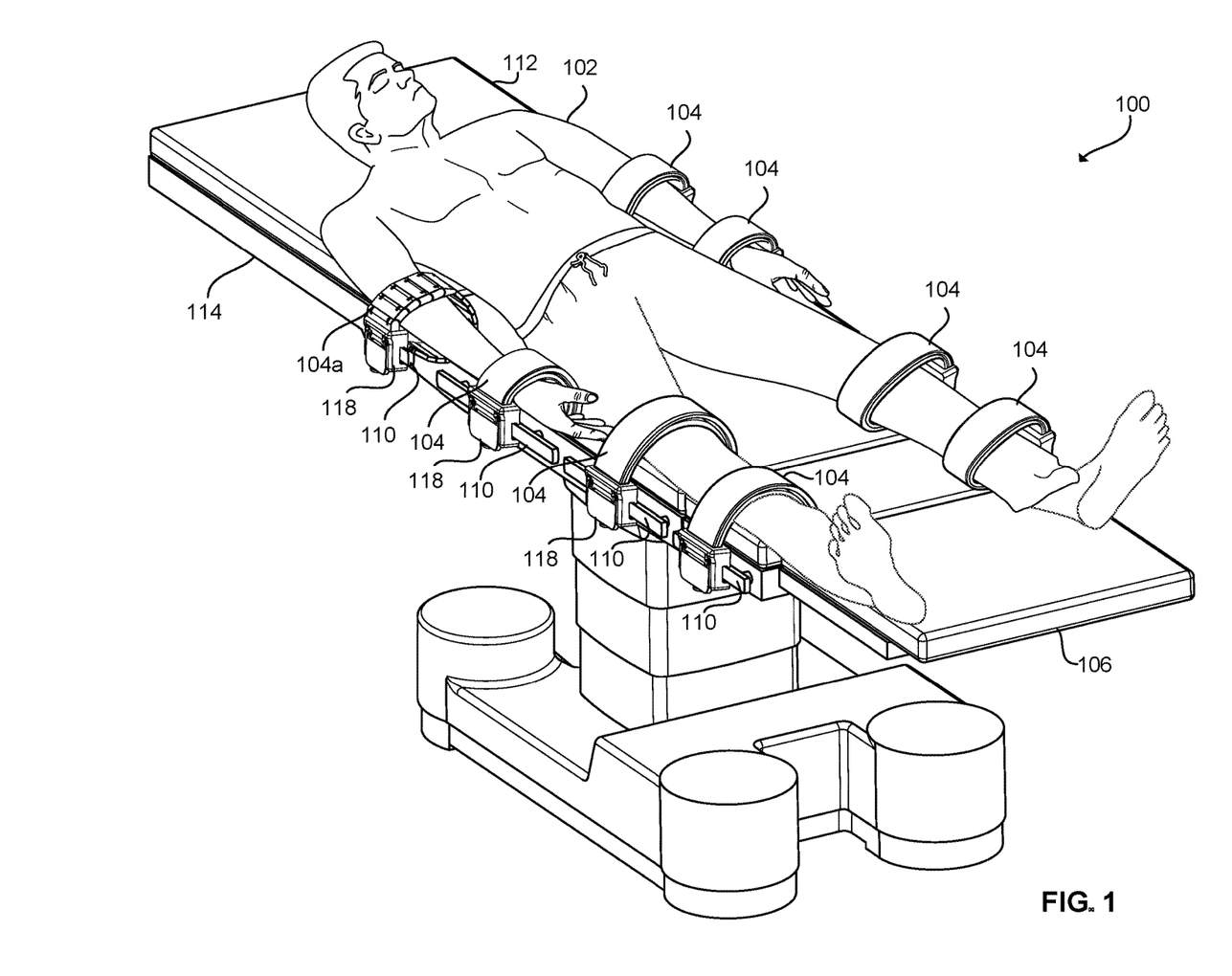
FIG. 1 shows a perspective view of an example system for positioning a patient, consistent with some embodiments of this disclosure.

Referring to FIG. 1, some embodiments of a system 100 for releasably maintaining a subject, such as a patient 102 that is sedated or otherwise prepared for medical assistance, in a selected position can include adjustable restraint devices 104 and a surgical table 106. In the depicted embodiment, the adjustable restraint devices 104 are adjustable limb restraints that are removably mated with portions of the surgical table 106 and that are manually adjustable to any of a variety of curved or other customized shapes for improved and comfortable engagement with limbs of the patient 102. As detailed below, the adjustable restraint devices 104 of the system 100 can releasably lock into the customized shape to safely hold the patient 102 in the selected position on the surgical table 106, which may reduce the likelihood of the patient 102 inadvertently moving out of the selected during a medical procedure.

The surgical table 106 can include one or more rails 110 that extend along each side of the surgical table 106. The one or more rails 110 can extend from each side of the surgical table 106. In some aspects, each side of the table 106 can include a plurality of rails 110 that are spaced apart along the length of the surgical table 106, while in other aspects, each side of the surgical table 106 can include a continuous rail 110 that extends along the length of the surgical table 106. For example, a left side 112 of the surgical table 106 can include four rails 110 spaced apart along the length of the surgical table 106, and a right side 114 of the surgical table 106 can include four rails 110 spaced apart along the length of the surgical table 106.

In the depicted embodiment, the system 100 includes a plurality of the adjustable restraint devices 104 that are slidably mated to the surgical table 106. Each adjustable restraint device 104 is adjustable and can be formed as a flexible cuff system to extend around a patient's limb (e.g., an arm, a leg, or a torso of a patient). Each adjustable restraint device 104 can be independently operable by a user so that each restraint device 104 can be separately controlled by a user as desired. As illustrated, the system 100 includes adjustable restraint devices in the size and form of adjustable limb restraints 104 positioned and formed around the arms and the legs of the patient 102. In the depicted embodiment, the system 100 includes two adjustable limb restraints 104 for each arm of the patient 102 and two adjustable limb restraints 104 for each leg of the patient 102. In other embodiments, the system 100 can include an adjustable limb restraint 104 for each limb of the patient 102. In other examples, the system 100 can include adjustable limb restraints 104 for the arms and not the legs or adjustable limb restraints 104 for the legs and not the arms.

Still referring to the depicted embodiment in FIG. 1, a first portion of the adjustable limb restraints 104 is positioned on the right side 114 of the surgical table 106, and a second portion of the adjustable limb restraints 104 is positioned on the left side 112 of the surgical table 106. In this embodiment, the system 100 includes four adjustable limb restraints 104 on the right side 114 and four adjustable limb restraints 104 on the left side 112. While four adjustable limb restraints 104 on each side of the surgical table 106 is shown, the system 100 is not limited to this arrangement. The system 100 can include one adjustable limb restraint 104, two or more adjustable limb restraints 104, or a plurality of adjustable limb restraints 104. The adjustable limb restraints 104 depicted in FIG. 1 preferably include a protective outer sleeve (described in more detail below) to provide a padded interface with the patient and to protect the interior mechanism of each adjustable limb restraint 104, but one adjustable limb restraint 104a is depicted in FIG. 1 with the protective sleeve removed from view for illustrative purposes. In some implementations, the protective sleeve is slidably removable from the adjustable limb restraint 104 so that the sleeve can be readily discarded in a sanitary manner after its use, and the remaining components of the adjustable limb restraint 104 can be receive a new protective sleeve for reuse in subsequent medical procedures.

In some embodiments, each of the adjustable limb restraints 104 can removably connect to one of the rails 110 of the surgical table 106. For example, each adjustable limb restraint 104 includes a handle body 118 that defines a recess that is configured to slidably mate the adjustable limb restraint 104 with at least one of the rails 110. In use, the adjustable limb restraints 104 are movable along the rails 110 to a customized position relative to the surgical table 106 (e.g., to customize the longitudinal position for patients of different sizes or in different positions), where the adjustable limb restraints 104 can be releasably locked into its selected position along the rail 110 during the medical procedure.

Figure 2A:
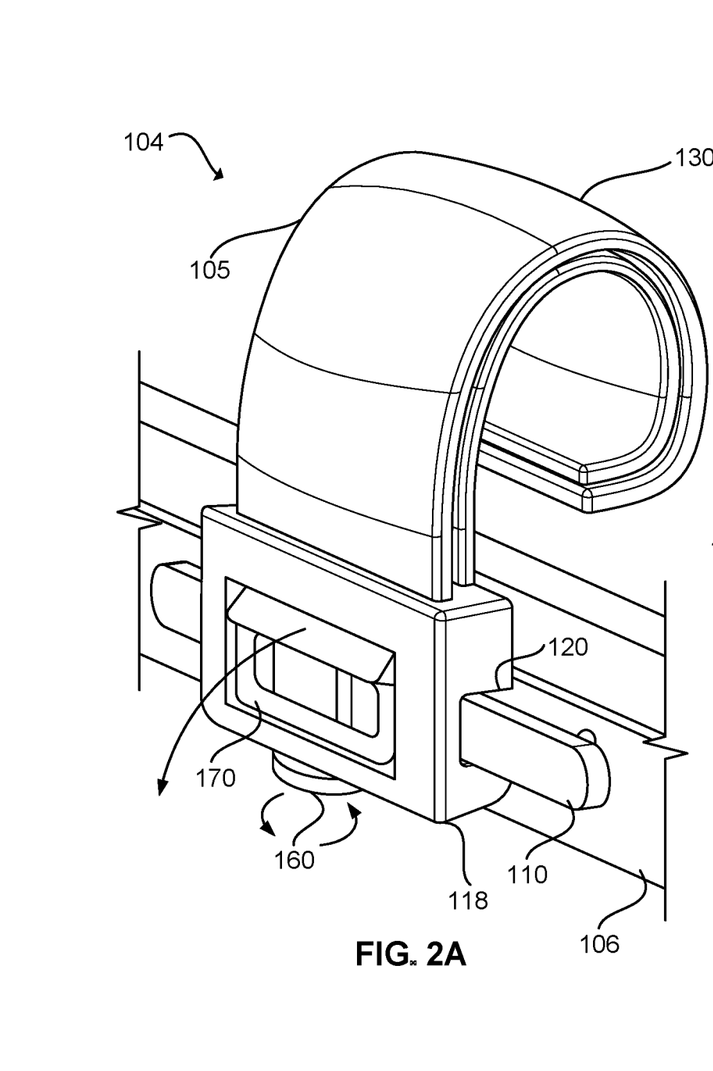
FIG. 2A shows a perspective view of an example adjustable limb restraint connected to a surgical table of the system of FIG. 1.
Figure 2B:
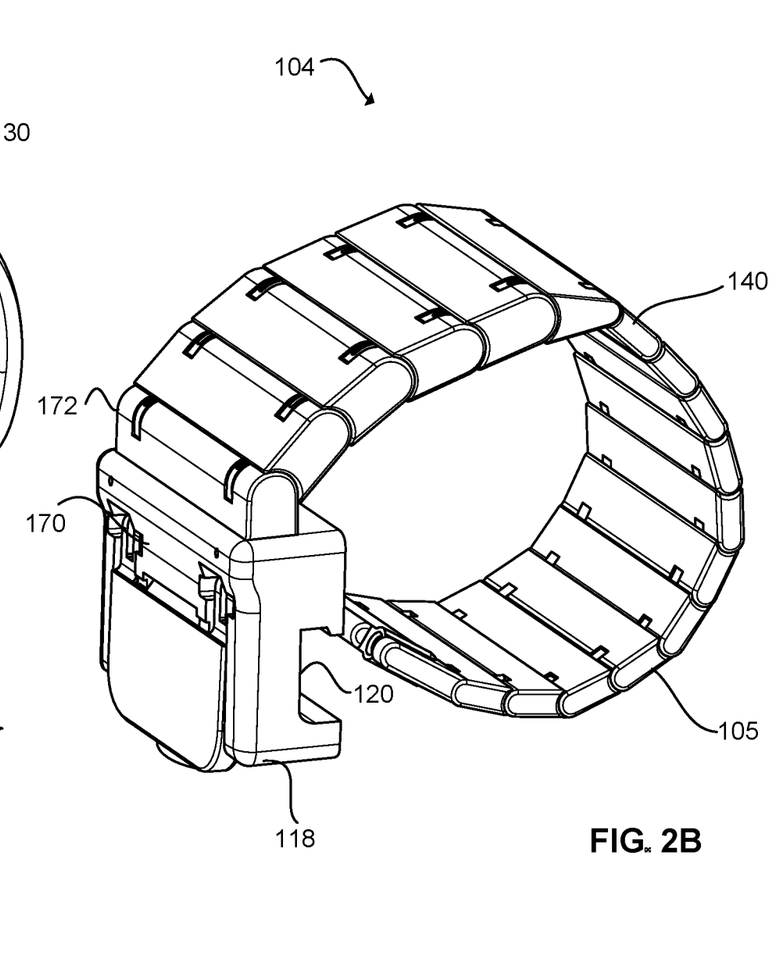
FIG. 2B a perspective view of the adjustable limb restraint of FIG. 2A with a protective sleeve removed from view.

Referring now to FIGS. 2A-B, some embodiments of the adjustable restraint device 104 can include the protective sleeve 130 and an interior mechanism 140 to releasably lock the restraint device 104 in a curved or otherwise customized shape for comfortably engaging with a patient. FIG. 2A shows a perspective view of one of the adjustable limb restraints 104, which in this embodiment includes a flexible cuff body 105 extending distally from the handle body 118 toward a free end. The handle body 118 is connected to one of the rails 110 of the surgical table 106 of the system 100, as previously described in connection with FIG. 1. In this embodiment, the flexible cuff body 105 includes the protective sleeve 130 slidably positioned over an interior mechanism 140 (e.g., linkage assembly in this embodiment, as shown in FIG. 2B with the protective sleeve 130 removed from view for illustrative purposes) so as to provide a cushioned interface with the patient and to provide sterile protective cover over the mechanical components of the mechanism 140. The protective sleeve 130 can include padding that can prevent pinching between the series of links 140, and the protective sleeve 130 can include a fluid impermeable outer material to facilitate rapid cleaning or removal of bodily fluid from the adjustable limb restraint 104.

In this embodiment, the flexible cuff body 105 (including the protective sleeve 130 and the mechanism 140) has an adjustable shape and can be releasably locked into a selected shape or unlocked for manual manipulation of the linkage assembly 140 (and the sleeve 130 therewith) to a different shape. In the depicted embodiment, the flexible cuff body 105 is in a curved configuration that is configured to extend around a limb of a patient (e.g., an arm, a leg, or a torso of the patient 102). The flexible cuff body 105 can be adjusted into customizable orientations to retain a limb of the patient 102, and the customizable orientations can include several different configurations, as shown and described below. As detailed below, the overall shape of the flexible cuff body 105 can be releasably locked in the customized orientation to maintain its shape for maintaining the patient's position during a surgical procedure The handle body 118 of the adjustable limb restraint 104 is configured to releasably lock the adjustable limb restraint 104 at a selected longitudinal position along the corresponding rail 110. The handle body 118 defines a mating interface surface 120 that is dimensioned to receive the rail 110 and slidably engage with the rail 110. In some aspects, the mating interface surface 120 is formed as a recess (e.g., oriented parallel to the rail 110) in the handle body 118 on a table side of the handle body such that the rail 110 extends through recess 120 and remains in abutment with the handle body 118. In some aspects, the position of the adjustable limb restraint 104 along the rail 110 can be secured by an actuator of the handle body 118. For example, the handle body 118 can include a rotatable knob 160 (FIG. 2A), and the knob 160 can facilitate releasably locking the adjustable limb restraint 104 in a selected position along the rail 110. In this example, the adjustable limb restraint 104 can be slidably moved along the rail 110 via the interface between the rail 110 and the recess 120 to reach a selected longitudinal position along the rail 110. After reaching this position selected by the user, the knob 160 can be rotated to urge a shaft of the knob 160 (not shown) into an interference fit with the rail 110, thereby releasably locking the adjustable limb restraint 104 in the selected longitudinal position along the rail 110. To readjust the adjustable limb restraint 104 relative to the rail 110, the knob 160 can be rotated in an opposite direction (to loosen the knob 160), thereby allowing the slidably movement of the adjustable limb restraint 104 along the rail 110.

Still referring to FIGS. 2A-B, some embodiments of the adjustable restraint device 104 also include another actuator, which can be shifted by the user to releasably lock the mechanism 140 in a customized configuration. For example, in this embodiment, the adjustable limb restraint 104 includes an actuator in the form of handle 170 on the handle body 118, which can be pivoted to actuate a mechanical lock upon the series of links in the linkage assembly 140. As shown in FIG. 2B, the linkage assembly 140 extends from the handle body 118 in a direction away from the rail 110/recess 120 interface, and the series of links in the linkage assembly 140 are pivotably connected to one another so that the overall length of the linkage assembly 140 can be manually adjusted from a first position (e.g., a vertically straight configuration such as that of FIG. 3 or other shape that is oriented away from patient location on the surgical table 106) to a second position (e.g., curved or otherwise customized to wrap around a targeted portion of the patient). As such, the relatively rotational adjustment of the adjacent links in the series of links 140 extending away from the handle body 118 facilitates the ability for a user to change the angle of the adjustable limb restraint 104 (e.g., toward a non-parallel angle with respect to the side surface of the rail 110 and the surgical table 106) and to change the shape of the adjustable limb restraint 104 (e.g., toward a curved configuration in the depicted embodiment). Additionally or alternatively, the adjacent links in the series of links 140 can be linked together via movable joint that provides motion beyond a hinged connection, including for example, a pivot point connection or a ball-and-socket component to provide multiple degrees of freedom between the adjacent links in the series of links 140.

In the depicted embodiment, the handle actuator 170 of the handle body 118 can be used to shift the flexible cuff body 105 between the locked and unlocked positions. The handle 170 can be positioned on an exterior facing side of the handle body 118 so that the handle 170 is accessible to a user while the adjustable limb restraint 104 is connected to the surgical table 106. The handle 170 can control a tension element or other lock instrument that acts upon the series of links 140 extending from the handle body 118. In some aspects, the series of links 140 are connected to the handle body 118 via a base 172, which extends upwardly away from the mating interface 120 of the handle body 118.

The handle 170 is movable between an unlocked position (refer to FIG. 2A) and a locked position (refer to FIG. 2B). For example, the handle 170 can be shifted from the unlocked position (FIG. 2A) to the locked position (FIG. 2B) by grasping the handle 170 and pivoting it downwardly away from the base 172 and the initial link of the linkage system 140. When the handle 170 is in the unlocked position, the flexible cuff body 105 is manually adjustable to a user's selected position, such as the curved configuration depicted in FIG. 2B. For example, with the handle 170 in the unlocked position, a user can adjust the overall shape of the flexible cuff body 105 (and the configuration of the series of links 140) to achieve a customized configuration that fits with any patient among a variety of different patient sizes, different limb types, and different limb arrangements relative to the surgical table 106 (or, alternatively, to release away from the patient after use). In some aspects, the series of links 140 are each configured to pivot with respect to each other to provide for a plurality of degrees of freedom that user can form the series of links 140 into various shapes and sizes. When the handle 170 is shifted to the locked position, the flexible cuff body 105 is releasably locked in the customized configuration, such as the curved configuration depicted in FIG. 2B. For example, after the flexible cuff body 105 is maneuvered or adjusted by a user into a desirable customized configuration (while handle 170 is in the unlocked position), the flexible cuff body 105 can be locked and thereafter fixed in that customized configuration (by shifting the handle 170 to the locked position).

Accordingly, some embodiments of the adjustable limb restraints 104 can be releasably locked in a wide number of customizable positions according as desired by a user (e.g., a surgeon, a nurse, a physical therapist, a doctor, a surgical technician, or other user) to achieve a safe and comfortable apparatus for maintaining the patient's position on the surgical table 106. Examples of patient positions that can be maintained by the adjustable limb restraints 104 include, but are not limited to supine, prone, lateral decubitus, lateral recumbent.

Figure 3:
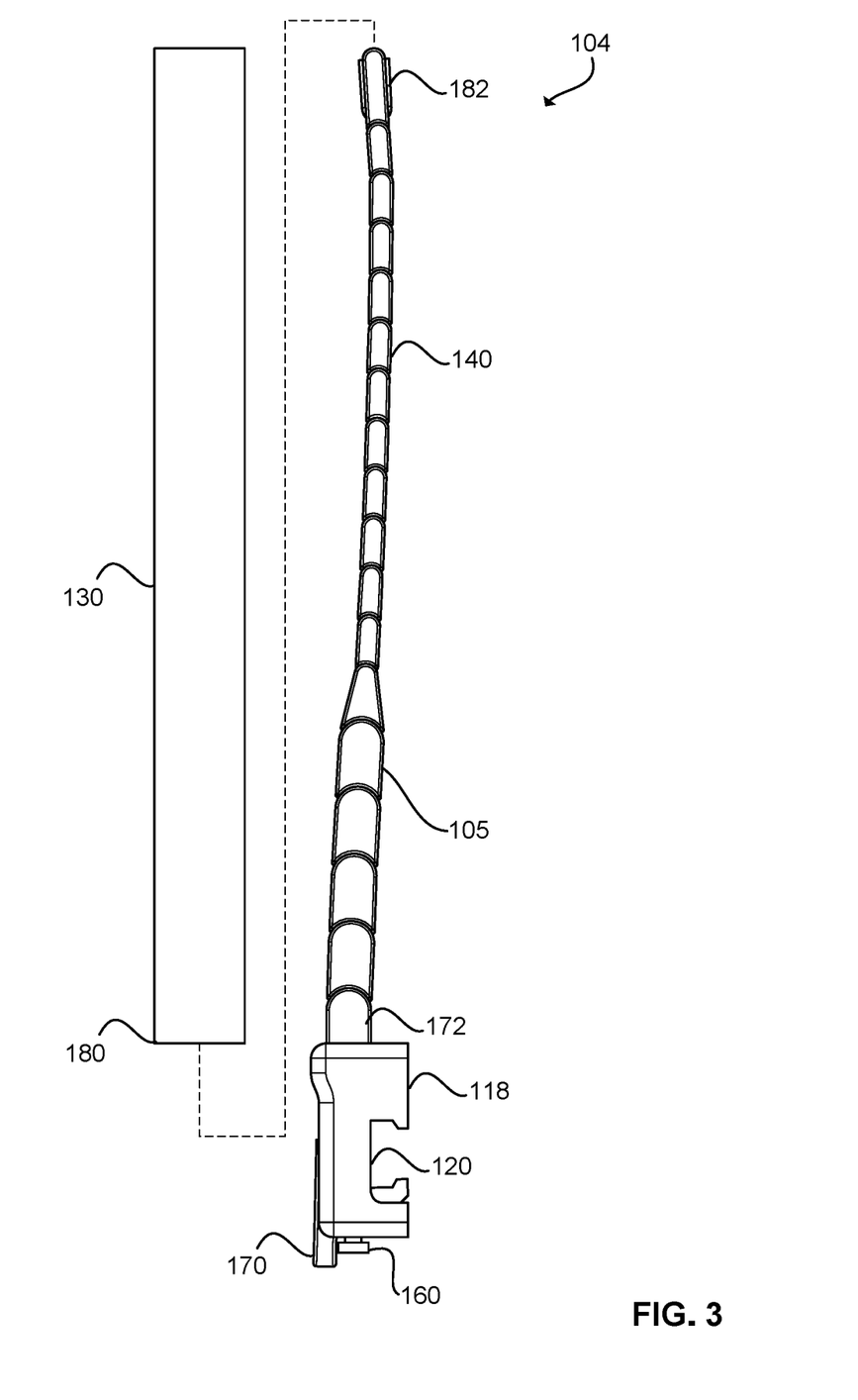
FIG. 3 shows an exploded side view of the adjustable limb restraint of FIGS. 2A-B.

Referring now to FIG. 3, some embodiments of the adjustable limb restraint 104 include a slidably removable form of the protective sleeve 130, which includes an interior pocket configured to receive the free end of the linkage assembly 140. The protective sleeve 130 can be a padded sleeve that extends around the series of links 140. For example, a proximal end 180 of the protective sleeve 130 can include an opening into the interior pocket space so that the protective sleeve 130 can be pulled over a distal-most end link 182 of the series of links 140. The protective sleeve 130 can be advanced over the series of links 140 until the proximal end 180 covers the base 172. As previously described, the protective sleeve 130 can include padding that can provide cushioning and comfort for the patient and furthermore prevent pinching between the series of links 140, and the protective sleeve 130 can include a fluid impermeable outer material to facilitate rapid cleaning of the adjustable limb restraint 104. In some circumstances, the protective sleeve 130 can remain on the adjustable limb restraint 104 during a cleaning or sterilization process, or in other implementations, the protective sleeve 130 can be removed from the adjustable limb restraint 104 for cleaning or sterilization. Additionally or alternatively, the protective sleeve is slidably removable from the linkage assembly 140 so that the sleeve 130 can be readily discarded in a sanitary manner after use with a first patient, and the remaining components of the adjustable limb restraint 104 can be receive a new protective sleeve for reuse in a subsequent medical procedure (e.g., with a different patient). As shown in FIG. 3, the adjustable limb restraint 104 can be arranged in the vertical configuration (extending upwardly away from the handle body 118) so that linkage assembly 140 extends away from the surgical table 106. This vertical configuration can facilitate insertion or removal of the protective sleeve 130. Additionally, in some circumstances, this vertical configuration can use temporarily employed while the patient is being loaded onto the surgical table, while the patient is being removed from the table, during a period of time of medical imaging in the area of the patient's limb near adjustable limb restraint 104.

Figure 4:
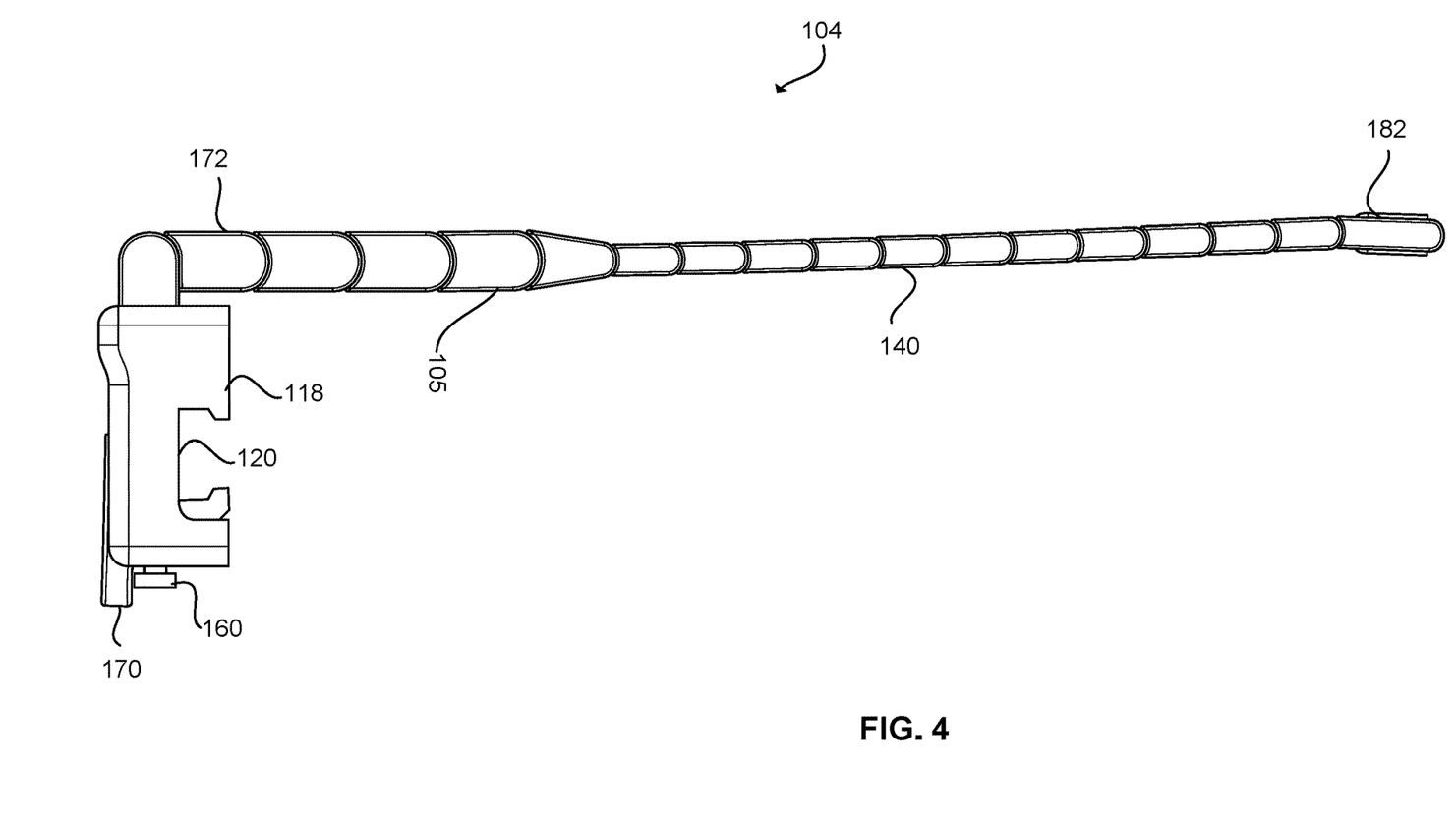
FIG. 4 shows the adjustable limb restraint of FIG. 3 in another position.

Referring now to FIG. 4, the adjustable limb restraint 104 (depicted with the protective sleeve removed from view for illustrative purposes) can be arranged in a horizontal configuration, in which the series of links in the linkage assembly 140 extend in a direction generally perpendicular to the configuration depicted in FIG. 3. In some aspects, the horizontal position of the adjustable limb restraint 104 can allow the adjustable limb restraint 104 to lie flat on the surgical table 106, for example, while that portion of the surgical table is unoccupied.

Figure 5A:
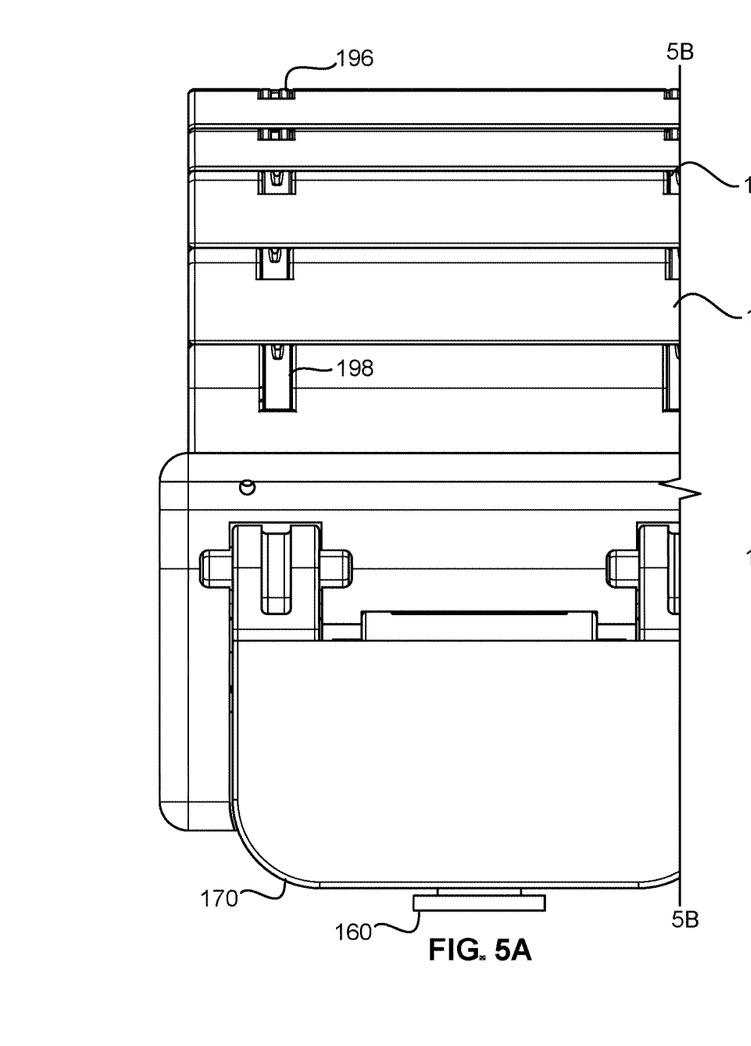
FIG. 5A shows a rear view of a section of the adjustable limb restraint of FIGS. 2A-B, with a section line 5B-5B.
Figure 5B:
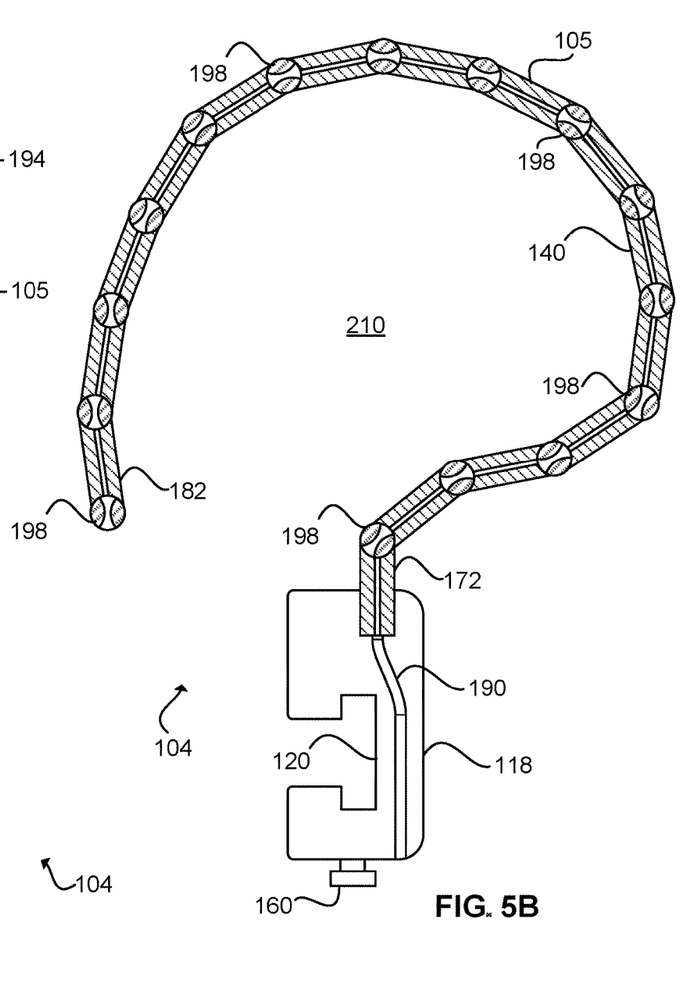
FIG. 5B shows a cross-sectional view the adjustable limb restraint along the section line 5B-5B from FIG. 5A.

Referring to FIGS. 5A-B, some embodiments of the adjustable limb restraint 104 can include one or more tensioners or lock instruments that engage with the series of links in the linkage assembly 140 to releasably lock the linkage assembly 140 in the selected position (in response to actuation of the handle 170). For example, the adjustable limb restraint 104 can include one or more cables 190 that extend from the handle body 118 through the series of links 140 of the flexible cuff body 105 and into the end link 182. In some aspects, the adjustable limb restraint 104 can include a single cable 190 that extends through the center of each link in the series of links 140. In the depicted embodiment, the adjustable limb restraint 104 can include two cables 190 (a right side cable 194 and a left side cable 196), and the two cables 190 may extend parallel to each other as they extend through the series of links 140. The right side cable 194 and the left side cable 196 can be offset equally from a central longitudinal axis of the linkage assembly 140 and also have the same offset from the respective left and right side edges of the linkage assembly 140.

In some aspects, each link of the series of links 140 includes one or more guide members 198 through which a respective cable 190 extends. The guide members 198 can include a disc, a bearing, a gasket, or a channel structure that facilitates the connection of the series of links 140 together and the extension of the one or more cables 190 through the series of links. Each link of the series of links 140 can include one or more guide members 198. For example, each link of the series of links 140 can include two guide members 198, with a guide member 198 positioned for the right side cable 194 and a guide member 198 positioned for the left side cable 196.

Referring to FIG. 5B and to FIGS. 2A-B, the handle 170 can be connected to the one or more cables 190 such that actuation of the handle 170 causes an adjustment of the one or cables 190. As such, the actuation of the handle 170 from the unlocked position to the locked position can urge the cables 190 to impart a force to the series of links in the linkage assembly 140 that locks the links in the selected position. For example, when the handle 170 is actuated to the locked position, the handle 170 can apply tension on the cables 190 to the urge the series of links 140 to compress toward one another to create a frictional engagement, thereby retaining each link in linkage assembly 140 in a fixed position relative to each adjacent link. When the handle 170 is shifted to the unlocked position, the tension in the cables 190 is released, thereby withdrawing the fixation caused by the frictional engagement between the links and allowing adjustment of the configuration of linkage assembly 140.

As previously described, the flexible cuff body 105 can be formed into various customizable shapes and sizes by manipulating the flexible cuff body 105 in the unlocked position. For example, the series of links 140 of the flexible cuff body 105 can define an opening 210 (FIG. 5B) sized to fit a patient's limb therein. Manipulating the flexible cuff body 105 into various shapes and sizes can adjust the overall shape and size of the opening 210. For example, as shown in FIG. 5B, the series of links 140 of the flexible cuff body 105 can be formed into an open ended hook that surrounds the opening 210. The open ended hook can begin at the base 172 and terminate at the end link 182. The open ended hook can extend vertically at the base 172 and can turn outwardly (i.e. away from the table side) to extend the opening 210 away from the table side. The series of links 140 can extend in a curved pattern to terminate in the end link 182, where the end link 182 is positioned closer to or above the table (e.g., surgical table 106) and the base 172 is positioned slightly lower than the end link 182.

While an open ended hook configuration is shown in FIG. 5B, various other configurations of the flexible cuff body 105 can be formed. For example, FIG. 1 shows the adjustable limb restraints 104 formed in closed-end loop configurations where the adjustable limb restraints 104 form a closed-end loop with the adjustable limb restraint 104 or with the surgical table 106. The closed loop can prevent a patient's limb from slipping out of the adjustable limb restraints 104. FIGS. 3 and 4 illustrate other configurations (e.g., vertical and horizontal configurations) of the adjustable limb restraints 104. Other example configurations include, but are not limited to, a conical shape where one end of the series of links 140 may have a smaller diameter than the other. In some examples, the adjustable limb restraint 104 can include several (e.g., 4-6, or more) smaller loosely connected individual linkage systems that could be manipulated to fit a patient's limb more closely.

Figures 6A, 6B, 6C:
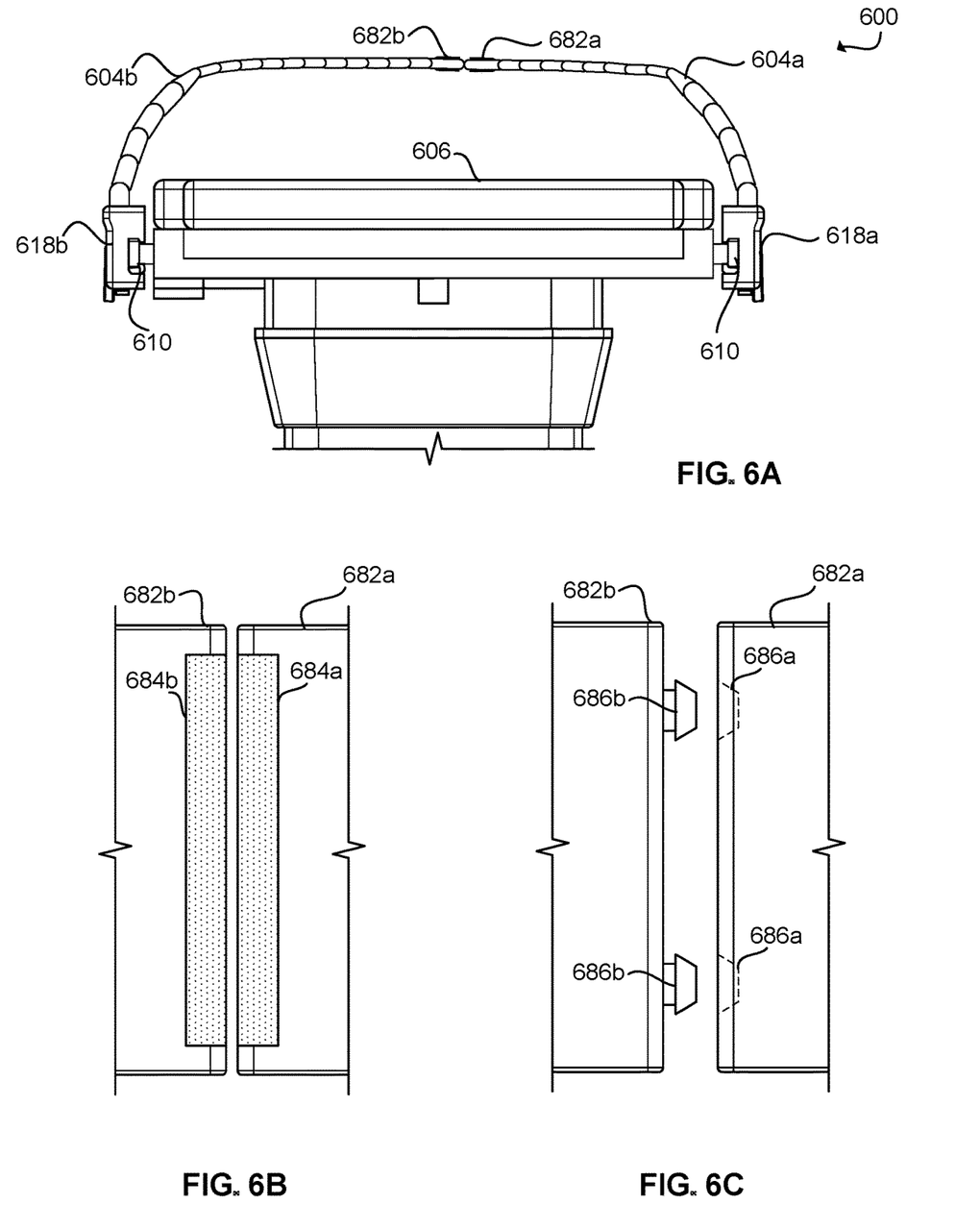
FIG. 6A shows an end view of another example system for positioning a patient using adjustable limb restraints, in accordance with some embodiments of this disclosure.
FIG. 6B shows a top view of an example section of an adjustable limb restraint of the system of FIG. 6A.
FIG. 6C shows a top view of another example section of an adjustable limb restraint of the system of FIG. 6A.

FIG. 6A shows an end view of another example system 600 for positioning a patient. In the illustrated embodiment, the system 600 includes a first adjustable limb restraint 604a on a first side of a surgical table 606 and a second adjustable limb restraint 604b on a second (opposite) side of the surgical table 606. In the depicted embodiment, the protective sleeve (described above) for each restraint device 604a, 604b is removed from view for illustrative purposes. Each adjustable limb restraint 604a and 604b can share features with the adjustable limb restraints 104 described in detail above. For example, each adjustable limb restraint 604a, 604b can include a handle body 618a, 618b that connects to a corresponding rail 610 of the surgical table 606. As shown in FIG. 6A, the adjustable limb restraints 604a and 604b are sized and positioned to extend over the surgical table 606 so that the respective free ends meet one another. Optionally, the protective sleeve for each adjustable limb restraint 604a, 604b can provide distal end access to fasteners positioned at an end link 682a, 682b (refer also to FIGS. 6B-C) of each adjustable limb restraint 604a, 604b. Accordingly, the free ends of the opposing limb restraints 604a, 604b can be secured to one another, the adjustable limb restraints 604a, 604b can extend across the surgical table 606 and over a torso of the patient to releasably secure the patient in a selected position on the surgical table 606.

As shown in FIGS. 6B-C, the end links 682a, 682b of the opposing the adjustable limb restraints 604a, 604b can be configured to secure with one another via magnetic or mechanical connections. For example, in FIG. 6B, the end links 682a, 682b are configured to connect to each other via magnets 684a, 684b in each end link 682a, 682b. The magnets 684a, 684b provide a releasable connection between the end links 682a, 682b. Alternatively or additionally, as shown in FIG. 6C, the end links 682a, 682b are configured to connect to each other via fasteners 686a, 686b in each end link 682a, 682b. For example, the fasteners 686a can include a female receptacle and the fasteners 686b can include a male connector that is dimensioned to fit in the female receptacle of the fastener 686a. The fasteners 686a, 686b provide a releasable connection between the end links 682a, 682b.

Figure 7:
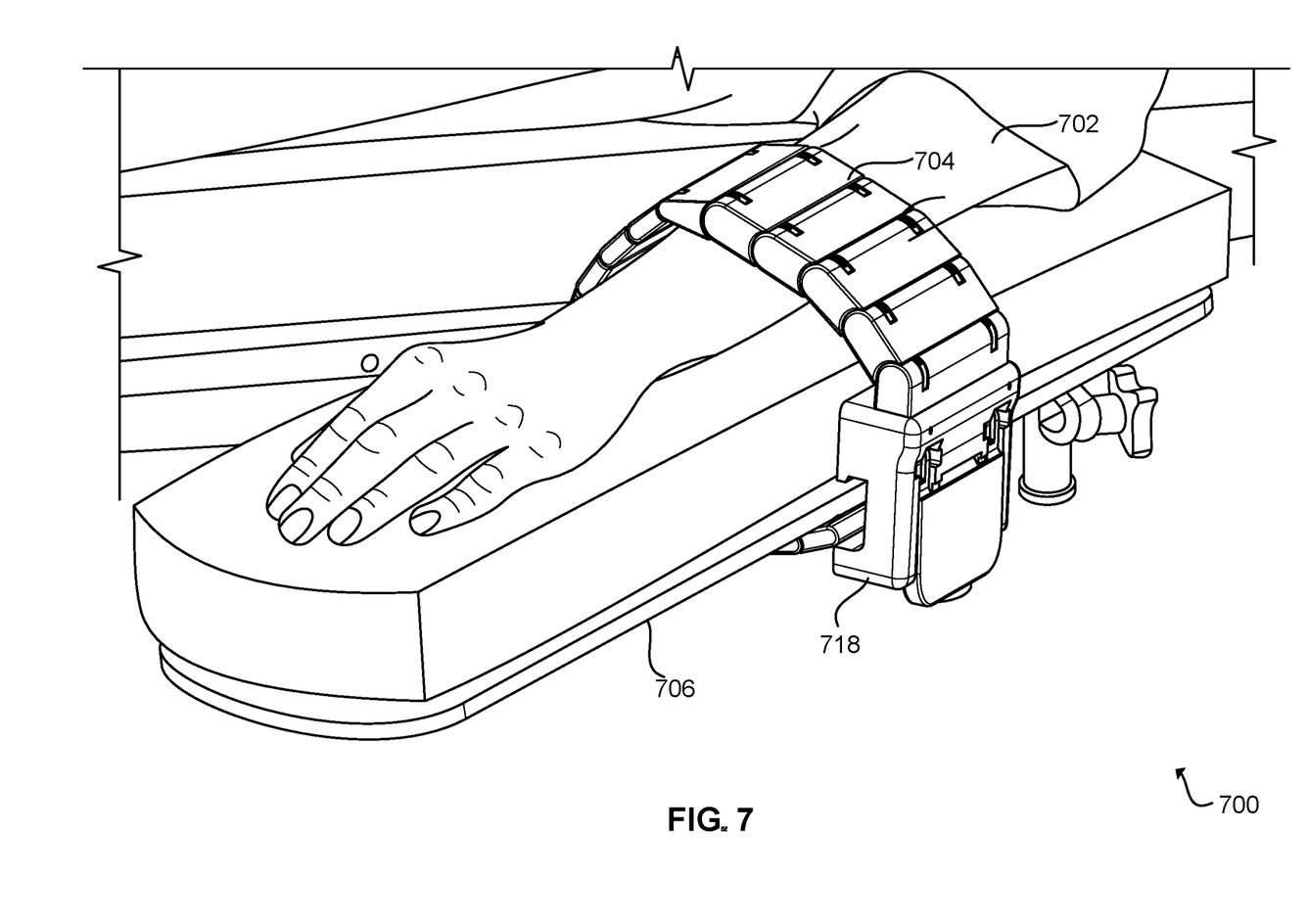
FIG. 7 shows a perspective view of another example system for positioning a limb of a patient on a surgical arm board, in accordance with some embodiments of this disclosure.

Referring now to FIG. 7, some embodiments of a system 700 using one or more adjustable limb restraints 704 can be employed for positioning an arm 702 of a patient on a surgical arm board 706. In the depicted system 700, the one or more adjustable limb restraints 704 can share the features of the adjustable limb restraints 104, 604a, 604b described in detail above. A handle body 718 (similar to body 118) of the adjustable limb restraint 704 can connect to the surgical arm board 706 to provide releasable engagement with the arm board 706, and the handle body 718 can include a handle actuator (similar to actuator 170) to shift between an unlocked and locked position to thereby releasably lock the linkage assembly in a selected position around the patient's limb. The adjustable limb restraint 704 can extend around the patient's arm 702 and to secure the positioning of the arm 702 on the arm board 706. The adjustable limb restraint 704 can include a padded sleeve (e.g., similar to padded sleeve 130), which is removed from view in FIG. 7 for illustrative purposes.

Figure 8A:
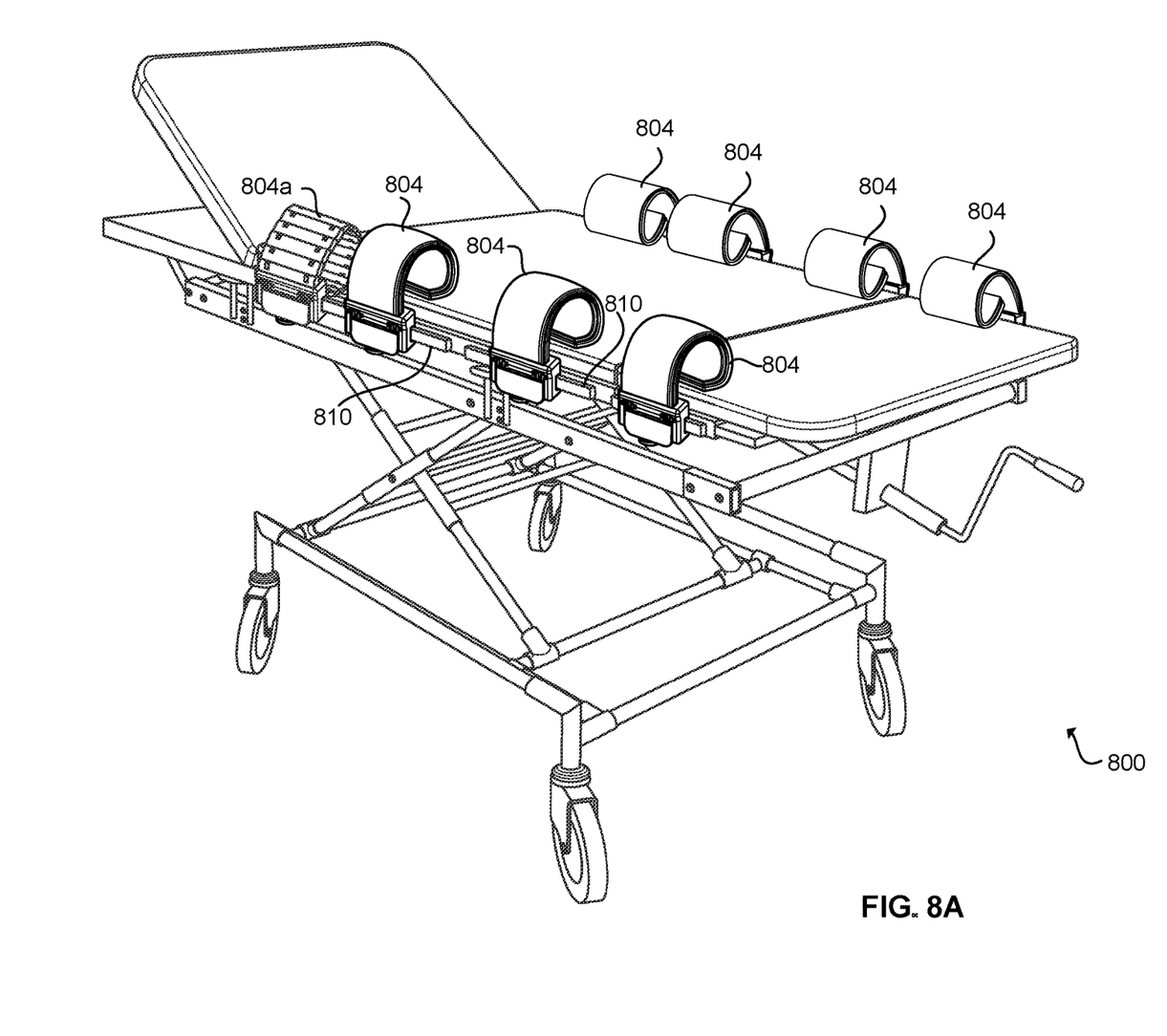
FIG. 8A shows a perspective view of another example system for positioning a patient relative to a medical transport apparatus, in accordance with some embodiments of this disclosure.
Figure 8B:
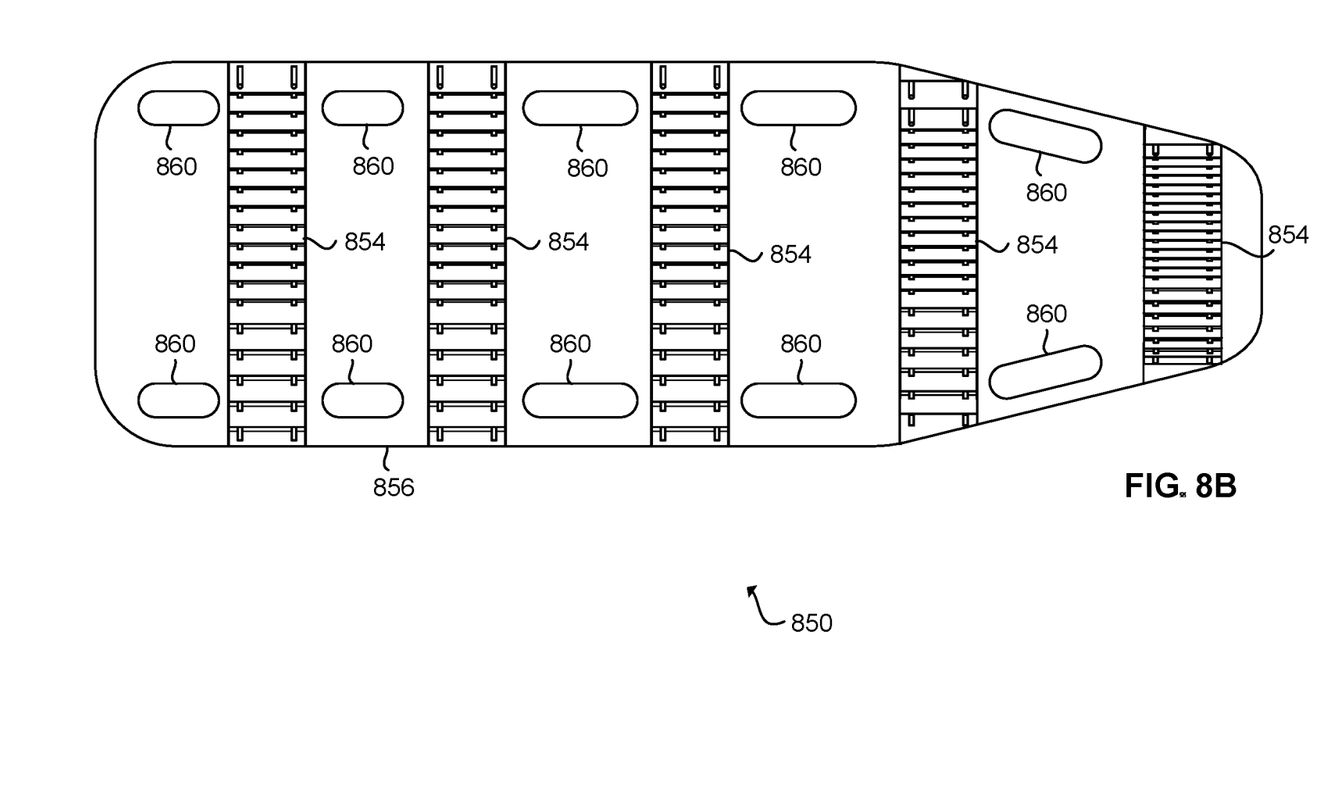
FIG. 8B shows a top view of a further example system for positioning a patient relative to another medical transport apparatus, in accordance with some embodiments of this disclosure.
Figure 9:
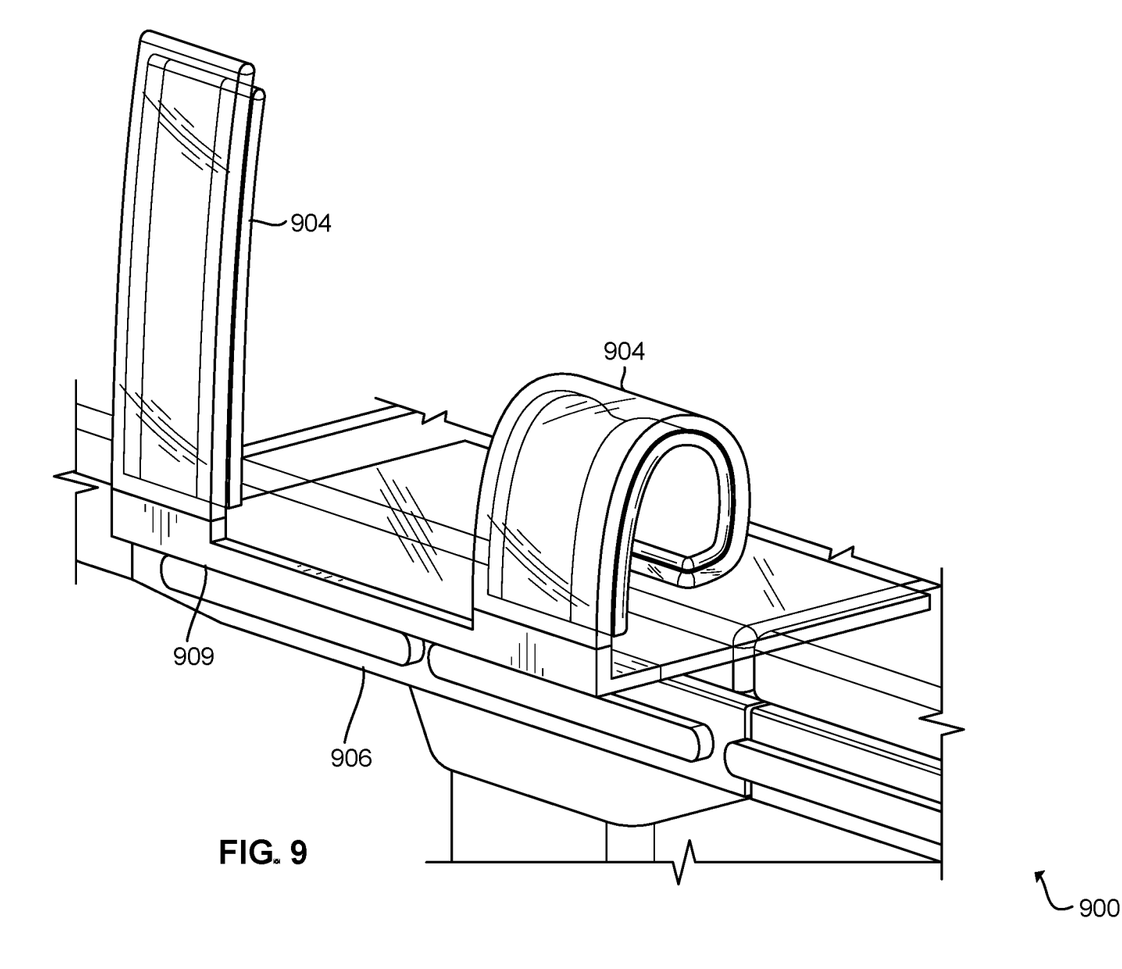
FIG. 9 shows a perspective view of another example system for positioning a patient, consistent with additional embodiments of this disclosure.

Referring to FIGS. 8A-B, some embodiments of the adjustable limb restraints can be used in systems 800, 850 to maintain a position of a patient relative to a medical transport apparatus. For example, as shown in FIG. 8A, the system 800 includes a portable stretcher 806 (e.g., for transport in and out of an ambulance vehicle or transport through a medical building) that has one or more adjustable limb restraints 804a and 804 that are connected to one or more rails 810 of the portable stretcher 806. The adjustable limb restraints 804a and 804 can share the features of the adjustable limb restraints 104a, 104, 604a, 604b described in detail above, including the handle body and linkage assembly operable to releasably lock in a customized configuration. The adjustable limb restraints 804 include the protective sleeve (similar to sleeve 130 described above), and the protective sleeve for adjustable limb restraint 804a is removed from view in FIG. 8A for illustrative purposes. In another example, as shown in FIG. 8B, the system 850 includes a stretcher board 856 (e.g., configured to receive a patient for transport via one or more users carrying the stretcher board) that has a set of adjustable limb restraints 854 connected side edges of the portable stretcher 856 (at longitudinal positions) between one or more handles 860. The adjustable limb restraints 854 can share the features of the adjustable limb restraints 104a, 104, 604a, 604b, 804 described in detail above, including the handle body and linkage assembly operable to releasably lock in a customized configuration. The adjustable limb restraints 854 can include a protective sleeve (e.g., similar to protective sleeve 130), which is removed from view in FIG. 8B for illustrative purposes Referring now to FIG. 9, some embodiments of a system 900 for positioning a patient can include one or more adjustable restraint devices 904 that use deformable internal wire structures to retain the customized shape of the cuff body. For example, each restraint system 904 can include deformable metallic wire structures that extend longitudinally within the padded outer body, and the deformable metallic wire structures are plastically deformable by a user so as to curl or bend to a customized configuration that engages with a patient's limb. As such, each adjustable restraint device 904 can be formed into various shapes to hold a patient in position on a surgical table or surgical transport device. Each restraint system 904 can include a padded cover that shares features with the protective sleeve 130 described above. In some aspects, the restraint systems 904 can include a mattress extension 909 that connects the restraint systems 904 together and extends under a mattress resting on a surgical table to connect the restraint systems to an operating table 906.

Figure 10A:
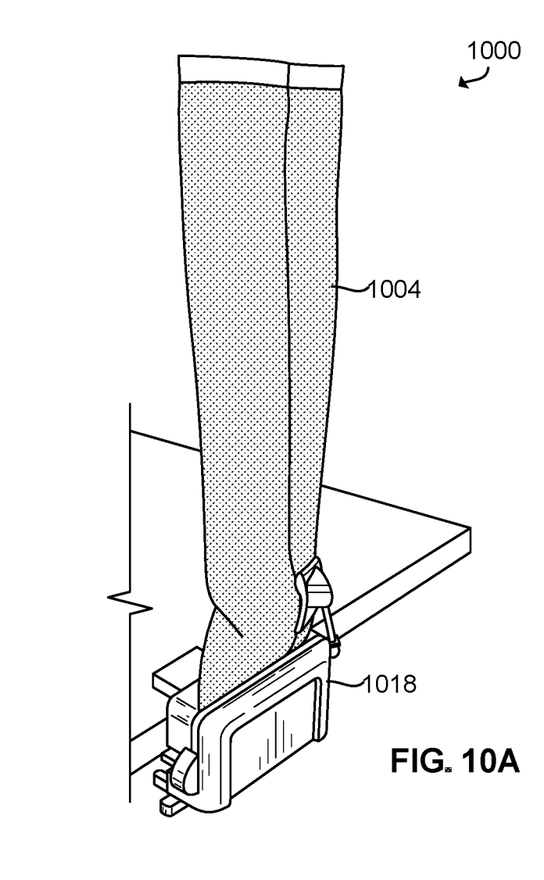
FIGS. 10A-B show perspective views of another example system for positioning a patient, in accordance with some embodiments of this disclosure.
Figure 10B:
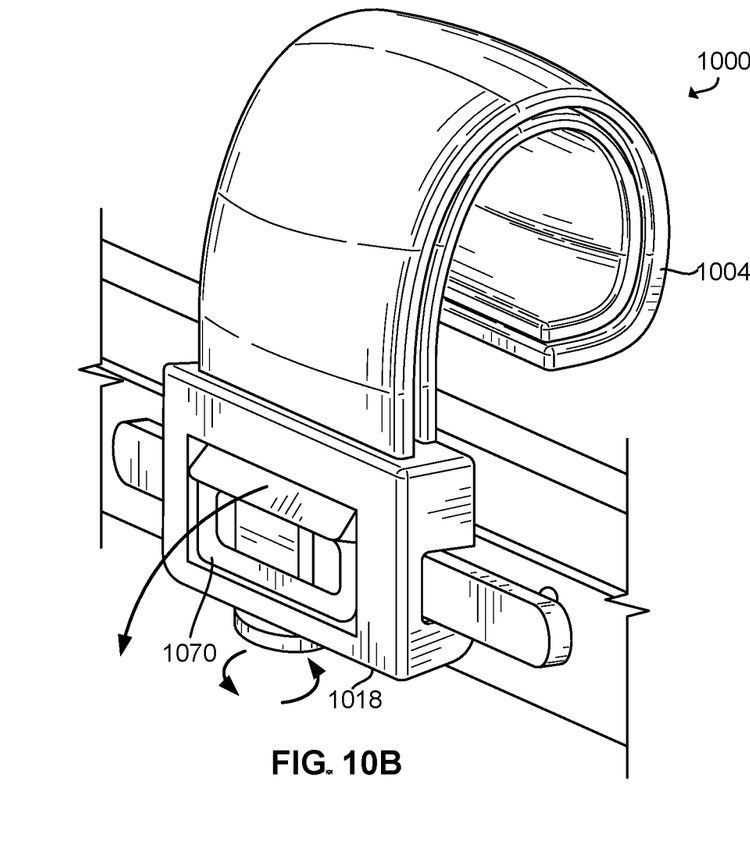

Referring now to FIGS. 10A-B, some embodiments for a system 1000 for positioning a patient can include one or more adjustable restraint devices 1004 that use vacuum pouch structures filled with foam material (e.g., foam pellets). In such embodiments, the vacuum pouch structures can be adjustable to a customized configuration (e.g., a curled configuration to engage with a patient's limb), and a vacuum source can be applied to an interior of the vacuum pouch structures to compress the foam material in the interior of the pouch and thereby retain the selected shape. Each of the adjustable restraint devices 1004 can include a handle body 1018 can connect the restraint systems 10004 to an operating table in a similar manner to handle body 118 described above. The handle body 1018 can include a handle 1070 that can be actuated to apply the vacuum source to the interior of the vacuum pouch structures. In some implementations, the handle actuator can be configured as a manual pump handle so that repeated actuations of the handle actuator will manually pump air out of the vacuum pouch structure and generate a vacuum therein to lock the adjustable restraint device 1004 in the selected configuration.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

Accordingly, other implementations are within the scope of the following claims.

What is claimed is:

1. A flexible cuff system for releasably maintaining a position of a patient, comprising:
   a flexible cuff body adjustable from a first orientation to a customized orientation to retain a limb in a selected position relative to a medical support substrate, the flexible cuff body including: a series of links that are adjustably connected to each other, and a fluid impermeable padded sleeve defining an interior pocket opened at one end to slidably mount the fluid impermeable padded sleeve over the series of links; and
   a handle body connected to a base portion of the flexible cuff body such that the base portion of the handle body extends in an upward direction above the handle body, the handle body including a handle cavity defined in a first side of the handle body and a handle that is movable between a locked position and an unlocked position in which a free end of the handle is received within the handle cavity, the handle body defining a mating interface surface in a second side of the handle body opposite from the handle cavity in the first side of the handle body to slidably engage the medical support substrate, and the handle body including a clamp actuator extending in a downward direction to a graspable position below both the mating interface surface and the handle cavity and being adjustable to releasably clamp the mating interface surface at a selected position along the medical support substrate;
   wherein, responsive to the handle being moved to the unlocked position, the flexible cuff body is adjustable from the first orientation to the customized orientation to extend around the limb, and
   wherein, responsive to the handle being moved to the locked position while the flexible cuff body is in the customized orientation, the flexible cuff body is locked in the customized orientation to retain the limb in the selected position relative to the medical support substrate.

2. The flexible cuff system of claim 1, further comprising first and second cables that extend from the handle body through the series of links of the flexible cuff body that are adjustably connected together and movable to a linked position relative to one another.

3. The flexible cuff system of claim 2, wherein each link comprises first and second guide structures through which the first and second cables respectively extend.

4. The flexible cuff system of claim 3, wherein the handle is connected to both the first and second cables, and responsive to the handle being moved to the locked position, the handle applies tension simultaneously to both the first and second cables to fix the series of links in the linked position relative to one another.

5. The flexible cuff system of claim 4, wherein responsive to the handle being moved to the unlocked position, the series of links are pivotable with respect to each other to adjust an overall shape of the series of links, each pivotable link in the series of links having a concave face at a proximal end and a convex face at a distal end.

6. The flexible cuff system of claim 5, wherein the flexible cuff body extends away from the handle body toward a free end of the flexible cuff body, and the free end of the flexible cuff body includes a fastener configured to connect to a second flexible cuff body.

7. The flexible cuff system of claim 5, wherein the medical support substrate is a surgical table, and the mating interface surface of the handle body configured to slidably engage with a rail of the surgical table.

8. The flexible cuff system of claim 5, wherein the medical support substrate is a stretcher, and the mating interface surface of the handle body configured to slidably engage with a side of the stretcher.

9. The flexible cuff system of claim 5, wherein the medical support substrate is an arm board extending from a surgical table, and the mating interface surface of the handle body configured to slidably engage with the arm board.

10. A system comprising:
    surgical table including one or more rails that extend along one or more sides of the surgical table;

a plurality of adjustable limb restraints releasably lockable at selectable positions along the one or more rails of the surgical table, each of the adjustable limb restraints including:

a flexible cuff body adjustable from a first orientation to a customized orientation to extend around and retain a limb in a customized position relative to the surgical table; and a handle body connected to a base of the flexible cuff body and defining a mating interface surface to slidably engage an adjacent rail of the one or more rails, wherein the base of the flexible cuff body extends in an upward direction away from both the mating interface surface of the handle body and the adjacent rail of surgical table, and the handle body including a handle pivotable between a locked position in which the handle extends in a downward direction below the adjacent rail and an unlocked position in which the handle extends in the upward direction above the adjacent rail;

wherein, responsive to the handle being moved to the unlocked position, the flexible cuff body is adjustable from the first orientation to the customized orientation to extend around the limb; and wherein, responsive to the handle being moved to the locked position while the flexible cuff body is in the customized orientation, the flexible cuff body is locked in the customized orientation to retain the limb in the selected position relative to the surgical table.

11. The system of claim 10, wherein the flexible cuff body comprises: a linkage assembly including a series of links that are adjustably connected to each other, and a fluid impermeable padded sleeve having an end opening sized to slidably receive a free end of the linkage assembly into an interior pocket of the fluid impermeable padded sleeve such that the fluid impermeable padded sleeve is slidably mounted over the series of links from the free end of the linkage assembly to the base of the flexible cuff body.

12. The system of claim 11, wherein responsive to the handle being moved to the unlocked position, the series of links are movable with respect to each other to adjust the flexible cuff body to the customized orientation shaped to extend around the limb.

13. The system of claim 12, wherein, responsive to the handle being moved to the locked position, the series of links are mechanically fixed relative to each other to releasably lock the flexible cuff body in the customized orientation.

14. The system of claim 11, wherein, responsive to the handle being moved to the unlocked position, the series of links are pivotable with respect to each other to adjust an overall shape of the flexible cuff body.

15. The system of claim 10 wherein a first set of the plurality of adjustable limb restraints are positioned on a first side of the surgical table and a second set of the plurality of adjustable limb restraints are positioned on a second opposite side of the surgical table.

16. The system of claim 10, wherein each of the plurality of adjustable limb restraints operate independently from one another.

17. The system of claim 10, wherein the flexible cuff body of each of the adjustable limb restraints comprises: a protective outer sleeve positioned over an interior mechanism including at least one of a linkage assembly, a deformable wire structure, and a vacuum pouch structure.

18. The system of claim 10, wherein each of the adjustable limb restraints is slidably mated to the one or more rails and releasably lockable to the one or more rails at a selected longitudinal position relative to the surgical table.

19. A method of maintaining a position of a patient, the method comprising:

releasably locking a handle body of an adjustable limb restraint to a rail of an operating table at a selected location relative to a limb of a patient on the operating table, wherein said releasably locking the handle body of the adjustable limb restraint to the rail comprises clamping a mating recess defined by a first side of the handle body to the rail by adjustment of a clamp actuator extending in a downward direction to a graspable position below both the mating recess and the rail;

adjusting a flexible cuff body of the adjustable limb restraint to a selected shape to engage with the limb of the patient, wherein said adjusting the flexible cuff body comprises pivoting a series of links of the flexible cuff body that are adjustably connected to each other and arranged within an interior pocket of a fluid impermeable padded sleeve that is opened at one end and slidable over of the series of links; and adjusting an actuator on the handle body of the adjustable limb restraint to releasably lock the flexible cuff body in the selected shape, wherein said adjusting the actuator on the handle body comprises pivoting a handle from an unlocked position in which a free end of the handle is received within a handle cavity defined in a second side of the handle body opposite from the mating recess in the first side of the handle body to a locked position in which free end of the handle extends in a downward direction below the handle cavity.

20. The method of claim 19, wherein in response to said adjusting the actuator on the handle body, the series of links are mechanically fixed relative to each other to releasably lock the flexible cuff body in the selected shape.

21. The method of claim 19, wherein the limb of the patient is an arm, leg, or torso of the patient.

* * * * *